(12) United States Patent
Rathert

(10) Patent No.: US 8,114,095 B2
(45) Date of Patent: Feb. 14, 2012

(54) INTRAOCULAR LENS INJECTION APPARATUS AND METHOD

(75) Inventor: Brian D. Rathert, Largo, FL (US)

(73) Assignee: Bausch & Lomb Incorporated, Rochester, NY (US)

( * ) Notice: Subject to any disclaimer, the term of this patent is extended or adjusted under 35 U.S.C. 154(b) by 837 days.

(21) Appl. No.: 11/595,739

(22) Filed: Nov. 10, 2006

(65) Prior Publication Data

US 2008/0114373 A1    May 15, 2008

(51) Int. Cl.
    *A61F 9/00*    (2006.01)
(52) U.S. Cl. .................................. 606/107; 623/6.12
(58) Field of Classification Search ............... 606/107; 623/6.12

See application file for complete search history.

(56) References Cited

U.S. PATENT DOCUMENTS

| 2002/0091360 A1* | 7/2002 | Peters, III ................ 604/198 |
|---|---|---|
| 2005/0154399 A1 | 7/2005 | Weber et al. |
| 2006/0142780 A1 | 6/2006 | Pynson et al. |
| 2006/0142781 A1 | 6/2006 | Pynson et al. |
| 2007/0060925 A1 | 3/2007 | Pynson |
| 2009/0125034 A1 | 5/2009 | Pynson |

FOREIGN PATENT DOCUMENTS

| WO | WO 2005003097 A1 * | 1/2005 |
|---|---|---|
| WO | WO 2005/030097 A1 | 4/2005 |
| WO | WO 2005030097 A1 * | 4/2005 |
| WO | WO 2006/071561 A1 | 7/2006 |

OTHER PUBLICATIONS

Bessiere et al., "U.S. Appl. No. 10/571,388, filed Sep. 26, 2003 (not published)."
BIC Round Stic, "Product Page, www.bicworld.com," (Feb. 14, 2007).

* cited by examiner

*Primary Examiner* — Gary Jackson
*Assistant Examiner* — Kevin Everage
(74) *Attorney, Agent, or Firm* — Jeffrey B. Powers

(57) ABSTRACT

An IOL injector comprising a distal body portion comprising a tip through which an IOL is injected into an eye, a tip protector, and a proximal body portion configured to connect to the distal body portion. The distal body portion and the tip protector being are configured to lockingly connect together, and the tip protector and proximal body portion are configured to interact with one another such that, when the tip protector and the distal body portion are in a connected state, the tip protector is unlocked from the distal body portion as the proximal body portion is being connected to the distal body portion.

8 Claims, 8 Drawing Sheets

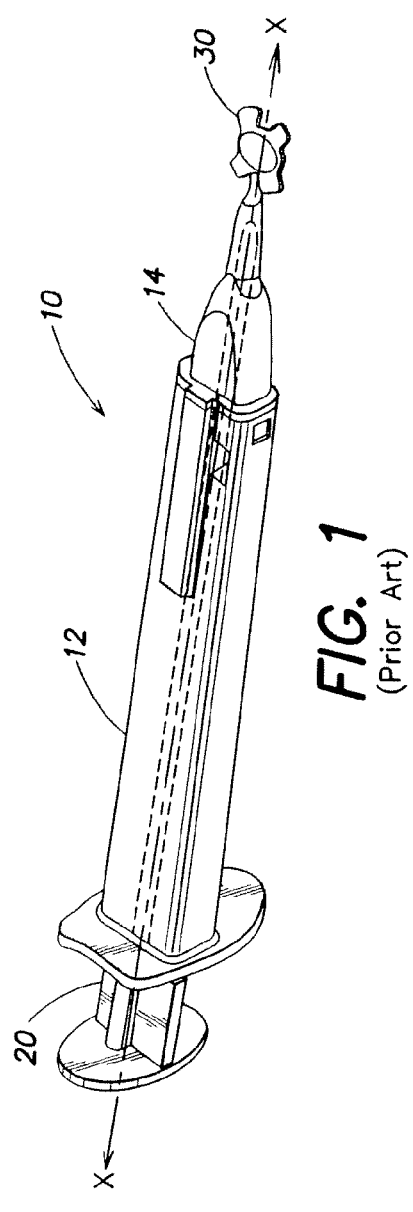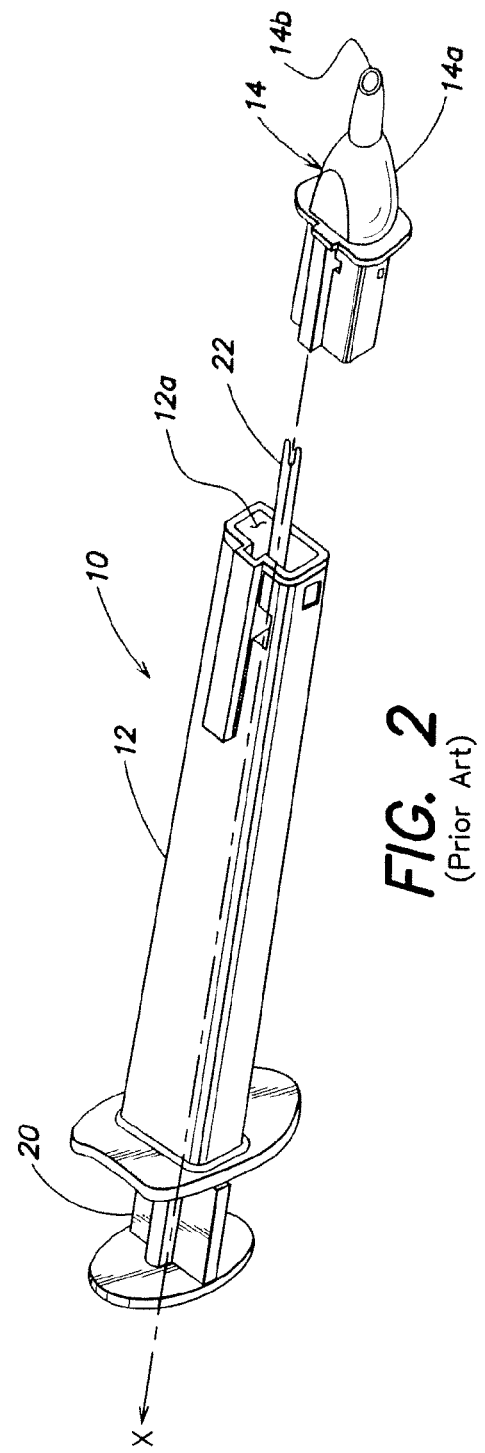
FIG. 1 (Prior Art)
FIG. 2 (Prior Art)

INTRAOCULAR LENS INJECTION APPARATUS AND METHOD

FIELD OF INVENTION

The present invention relates to methods and apparatus for protecting a tip of an intraocular lens (IOL) injector, and more particularly to methods and apparatus for protecting a tip of an intraocular lens (IOL) injector in which preparation for injection of an IOL is facilitated.

BACKGROUND OF THE INVENTION

IOLs are artificial lenses used to replace natural crystalline lenses of patients' when their natural lenses are diseased or otherwise impaired. Under some circumstances a natural lens may remain in a patient's eye together with an implanted IOL. IOLs may be placed in either the posterior chamber or the anterior chamber of an eye.

IOLs come in a variety of configurations and materials. Various instruments and methods for implanting such IOLs in an eye are known. Typically, an incision is made in a patient's cornea and an IOL is inserted into the eye through the incision. In one technique, a surgeon uses surgical forceps to grasp the IOL and insert it through the incision into the eye. While this technique is still practiced today, more and more surgeons are using IOL injectors, which offer advantages such as affording a surgeon more control when inserting an IOL into an eye and permitting insertion of an IOL through a smaller incision. Relatively small incision sizes (e.g., less than about 3 mm) are preferred over relatively large incisions (e.g., about 3.2 to 5+ mm) since smaller incisions have been attributed with reduced post-surgical healing time and reduced complications such as induced astigmatism.

In order for an IOL to fit through a small incision, it is typically folded and/or compressed prior to the injector entering the eye and depositing the lens, where the lens will assume its original unfolded/uncompressed shape. FIG. 1 is a perspective view of a fully-assembled, conventional, two-piece injector device 10 showing an IOL 30 being expressed from the tip of the device. The basic components of injector device 10 include a proximal body portion 12, a plunger 20, and a distal body portion 14.

FIG. 2 is a perspective view of two-piece injector device 10 with the two-pieces (i.e., a proximal body portion 12 and a distal body portion 14) being detached from one another. Typically, when using a two piece device, an IOL is loaded into one of the distal body portion and the proximal body portion. Subsequently, the proximal body portion and the distal body portion are assembled to ready the device 10 for delivery of the IOL.

When proximal body portion 12 and distal body portion 14 are attached together, plunger 20 can be moved through proximal body portion lumen 12a so that plunger tip 22 engages and pushes the IOL 30 through passageway 14a and out tip 14b (as shown in FIG. 1).

To deposit an IOL through a small incision, an injector as shown in FIG. 1 is provided with a commensurately small tip 14b through which the IOL enters the eye. Tips 14b having small features have been found to be susceptible to damage during shipping and during operating room activities.

Various structures have been suggested to protect the tip. However, such structures can be cumbersome for a doctor or operating room attendant to manipulate in preparation for depositing an IOL.

SUMMARY

Aspects of the present invention are directed to an IOL injector kit, comprising a distal body portion comprising a tip through which an IOL is injected into an eye, a tip protector (the distal body portion and the tip protector being configured to lockingly connect together), and a proximal body portion configured to connect to the distal body portion. The tip protector and proximal body portion are configured to interact with one another such that, when the tip protector and the distal body portion are in a connected state, the tip protector is unlocked from the distal body portion as the proximal body portion is being connected to the distal body portion.

In some embodiments, the distal body portion comprises a flange and the tip protector comprises at least one latch, the latch and flange being configured to lockingly connect the distal body portion and the tip protector together. The tip protector may comprise a side wall configured to enclose the tip. In some embodiments, the tip protector and the distal body portion are lockingly connected together.

Another aspect of the invention is directed to a method of preparing an IOL injector for insertion of an IOL, comprising unlocking a tip protector from a distal body portion by connecting a proximal body portion to the distal body portion. In some embodiments, the method further comprises lockingly connecting a tip holder to a distal body portion, prior to the step of unlocking. In other embodiments, the method further comprises lockingly connecting a tip holder to a distal body portion, after to the step of unlocking.

BRIEF DESCRIPTION OF THE DRAWINGS

Illustrative, non-limiting embodiments of the present invention will be described by way of example with reference to the accompanying drawings, in which the same reference number is used to designate the same or similar components in different figures, and in which:

FIG. 1 is a perspective view of a fully-assembled two-piece injector device showing an IOL expressed from the tip of the device;

FIG. 2 is a perspective view of a two-piece injector device with the proximal body portion and the distal body portion detached from one another;

DETAILED DESCRIPTION

Aspects of the present invention are directed towards an IOL injector kit, comprising a distal body portion, a tip protector configured to lockingly connect to the distal body portion, and a proximal body portion configured to connect to the distal body portion. The tip protector and proximal body portion are configured to interact with one another such that, when the tip protector and the distal body portion are in a connected state, the tip protector is unlocked from the distal body portion as the proximal body portion is being connected to the distal body portion.

Figure 3:
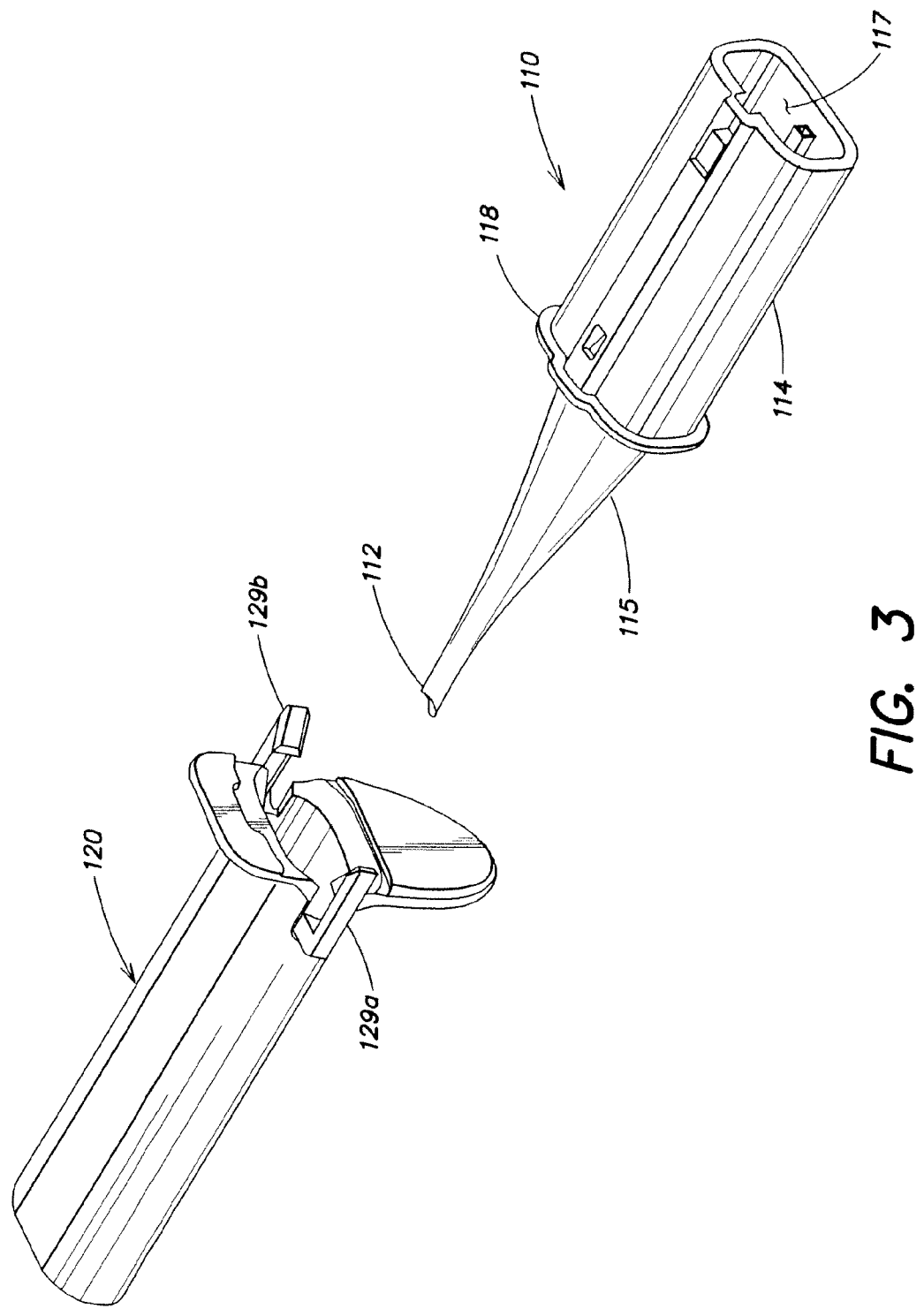
FIG. 3 is a perspective view of the distal body portion of a two-piece injector device, and a tip protector in an unconnected state.
Figure 5A:
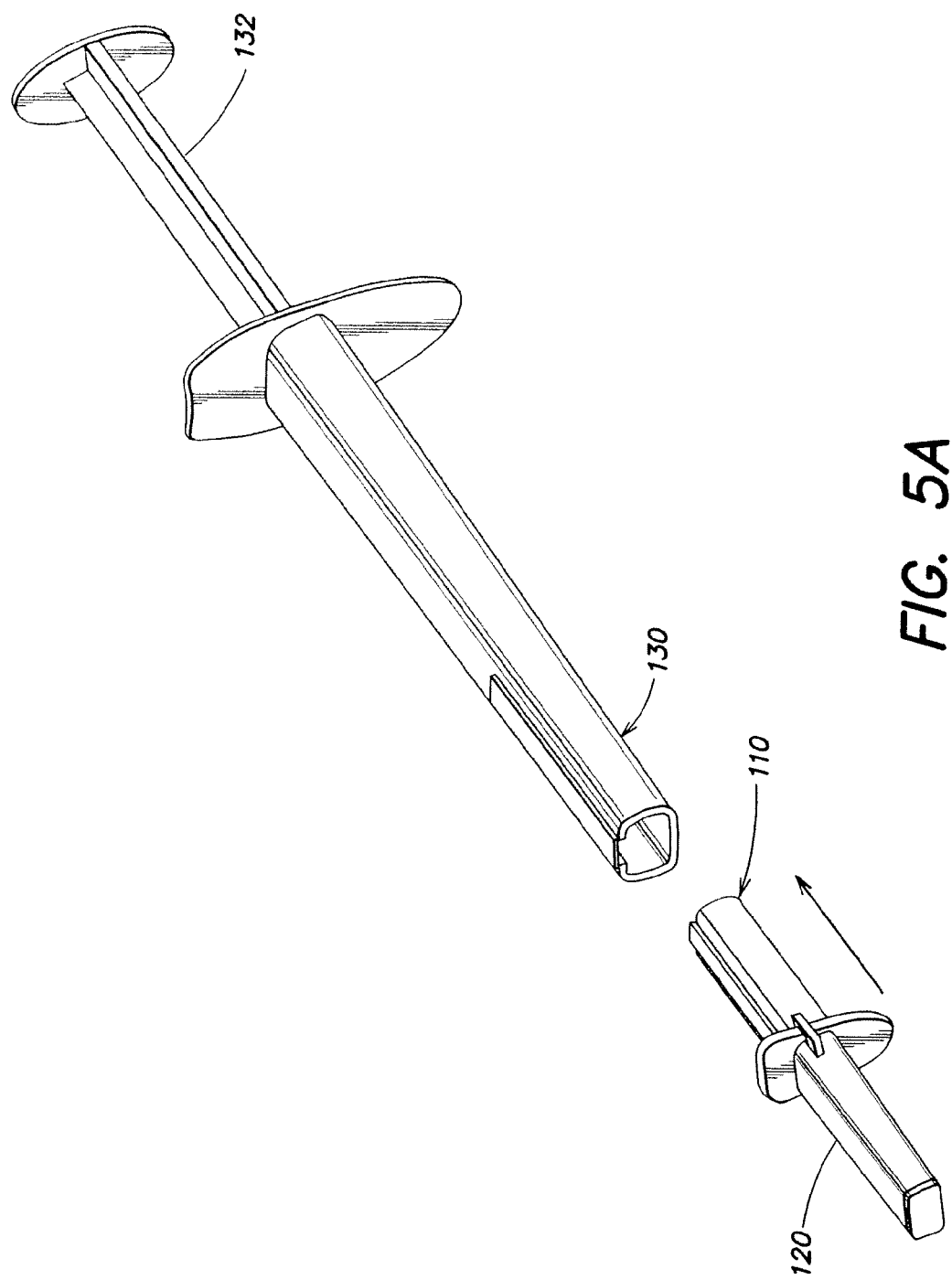
FIG. 5A is a perspective view of a connected distal body portion and tip protector as shown in FIG. 4A moving into engagement with a proximal body portion.

FIGS. 3 and 5A illustrate examples of parts constituting an embodiment of a kit according to aspects of the present invention. In particular, FIG. 3 shows an example of a distal body portion 110 and an example of a tip protector 120, and FIG. 5A shows an example of a proximal body portion 130.

Figure 4A:
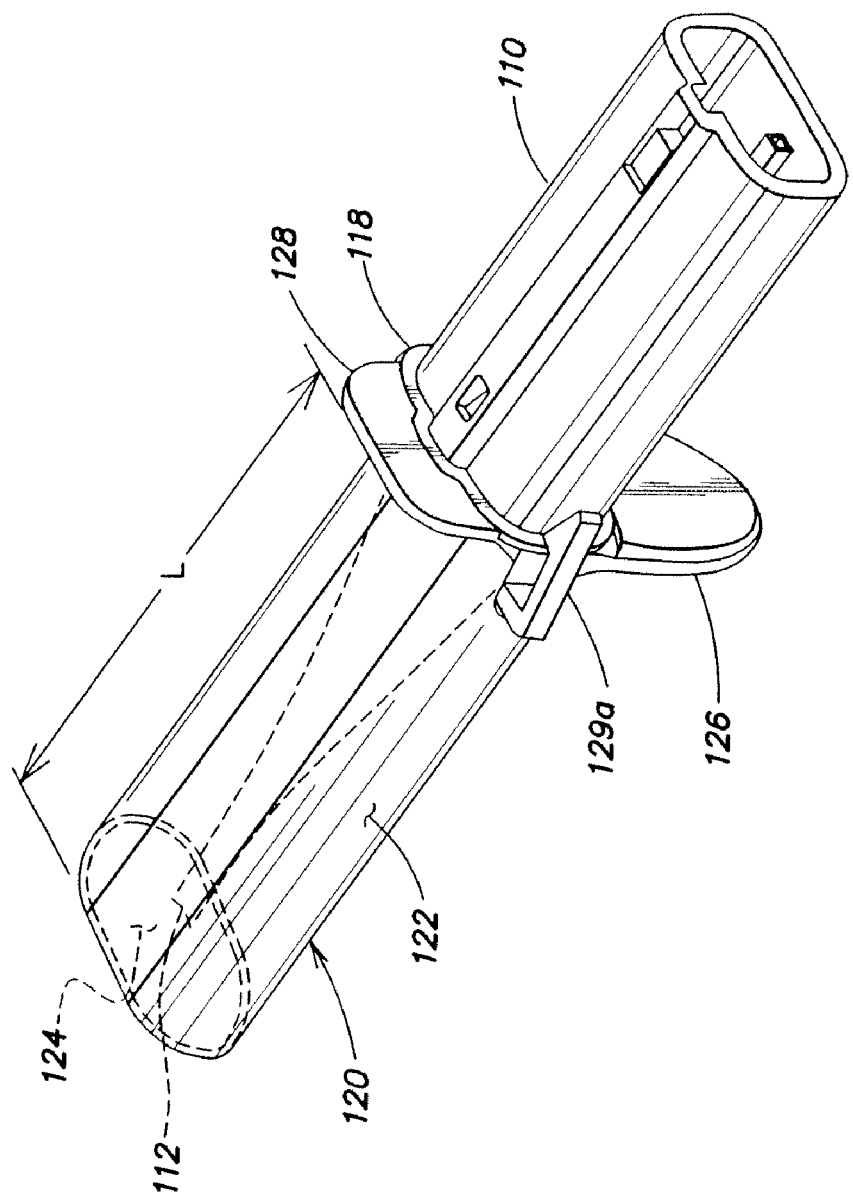
FIG. 4A is a perspective view of the distal body portion of FIG. 3 and the tip protector of FIG. 3 in a connected state.

Further aspects of the invention, including further details of the apparatus and methods of use, will now be discussed. FIGS. 3 and 4A are perspective views of a distal body portion 110 of an IOL injector device and a tip protector 120 shown in uncoupled and coupled states, respectively. According to aspects of the invention, the tip protector is configured to lockingly connect to the distal body portion. In the illustrated embodiment, distal body portion 110 includes a flange 118, and tip protector 120 includes latches 129a and 129b that lockingly connects to the flange. Although two latches are illustrated, in other embodiments, one latch or three or more latches may be included.

Figure 4B:
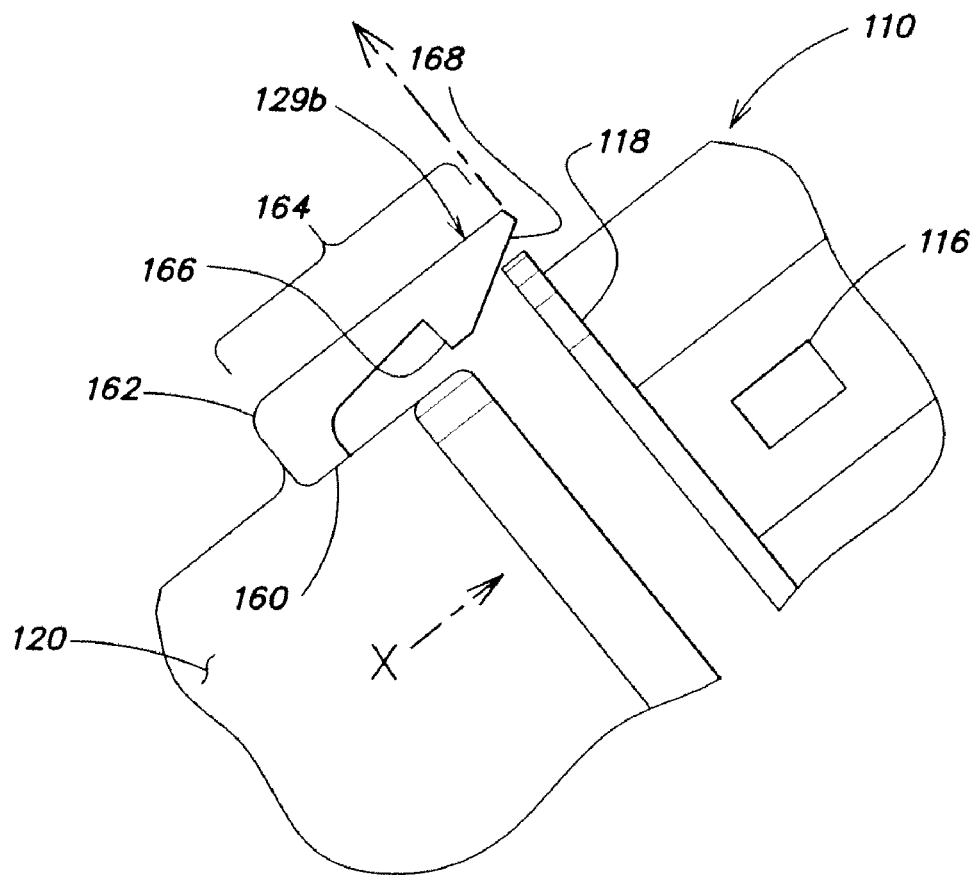
FIG. 4B is a partial, expanded top view of distal body portion and the tip protector of FIG. 3 in which a flange on the distal body portion is contacting the engagement surface of the latch on the tip protector, prior to connection of the distal body portion and the tip protector.

As defined herein, components in "locking connection" contact one another in a manner such that separation of the components cannot be achieved by mere translation of the components relative to one another. Rather, a portion of at least one of the components must be manipulated prior to separation. In FIG. 4B, flange 118 and latch 129b constitute a lock; and latch 129b is to be manipulated prior to separation of the tip protector and the distal body portion.

Figure 4C:
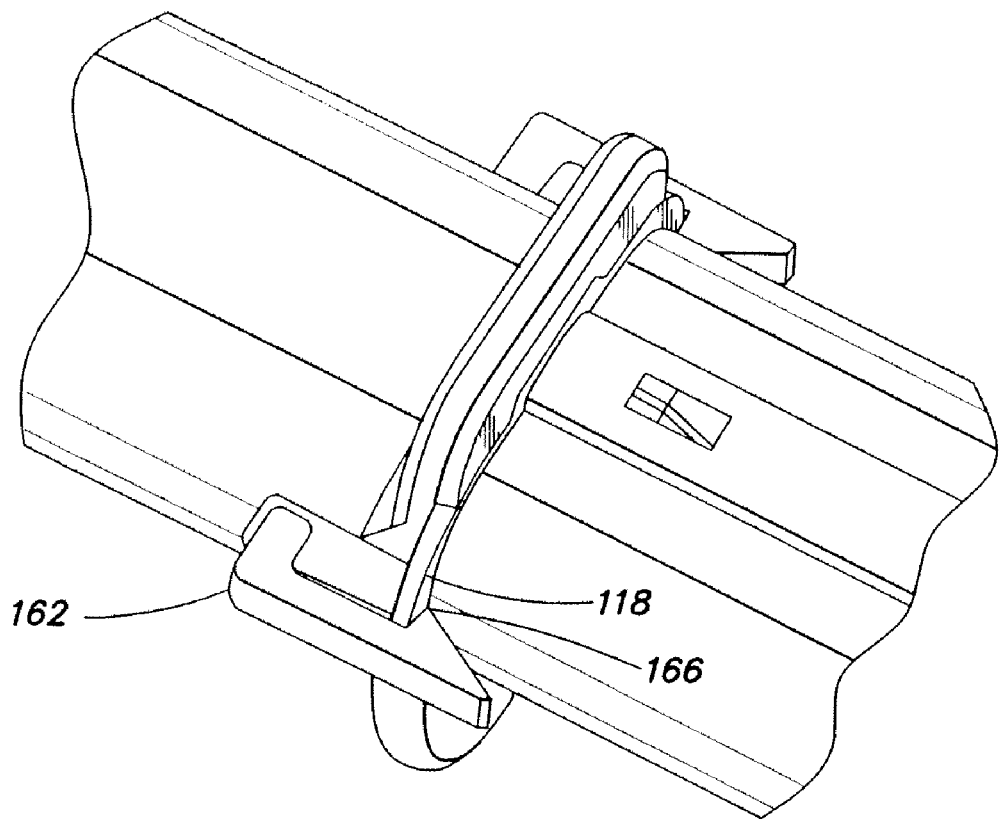
FIG. 4C is an expanded, perspective view of the connected distal body portion and the tip protector of FIG. 4A.

As illustrated in FIG. 4B, latch 129b extends from a wall of the tip protector at a location 160. Also as illustrated in FIG. 4B, flange 118 is contacting the engagement surface 168 of latch 129b on the tip protector. The latch 129b comprises an elongate section 164, a hinge portion 162, a hook 166 and an engagement surface 168. As tip protector 120 is translated in a direction X, engagement surface engages flange 118 and the elongate section 164 is flexed radially outward about hinge 162. Operation of latch 129a is substantially the same as latch 129b. As illustrated in FIG. 4C, after the tip protector is translated such that engagement surface 168 passes flange 118, elongate section 164 attains an unstressed state and tip protector 120 is locked to distal body portion 110.

Referring to FIG. 3, in the illustrated embodiment, distal body portion 110 includes a loading station 114 in which a IOL is received through lumen 117, a compression zone 115 that is used to compress and/or fold an IOL to fit into an incision of the cornea, and a tip 112 through which an IOL is delivered to an eye.

It is to be appreciated that a distal body portion for use in embodiments of the present invention need not include a compression zone. For example an inserter may include a compressor drawer (not shown) in the IOL loading area to compress an IOL, or an IOL may be folded prior to loading the IOL into the inserter. Although the illustrated embodiment is loaded by locating an IOL in the loading station through lumen 117, injectors according to aspects of the invention can be designed to be loaded with an IOL using any suitable technique. For example, an IOL may be loaded into the proximal body portion through a lumen, or may be loaded into either the distal body portion or the proximal body portion through an opening in a sidewall. It is to be appreciated that loading through a sidewall may be achieved prior to or after connecting of the proximal body portion to the distal body portion.

As shown in FIG. 4A, tip protector 120 comprises a sidewall 122 having a length L that is great enough to extend beyond tip 112 thereby protecting the tip from side impact. In the illustrated embodiment, the tip protector has an end plate 124 so that tip 112 is fully enclosed by the tip protector. In the illustrated embodiment, tip protector 120 includes a tab 126 to facilitate handling of the tip protector, and stand 128 to facilitate placement of the tip protector (and distal portion) on a flat surface.

It is to be appreciated that tip protector 120 could be connected to distal body portion 110 in an operating room prior to manipulation of the inserter by operating room attendants. Accordingly, tip 112 is protected, prior to insertion, while the inserter is handled by one or more persons prior to an operation to insert an IOL. Alternatively, tip protector 120 could be connected to a distal body portion 110 during manufacturing or packaging stages at a manufacturing facility. In applications where the tip protector is connected to the distal body portion during manufacturing or packaging, the tip is protected during all subsequent handling, including during shipping. According to aspects of the invention, in the manner described below, a tip protector can be easily removed by an operating room attendant (who may be wearing gloves) prior to injection of an IOL.

FIG. 5A is a perspective view of the distal body portion 110 and the tip protector 120 as shown in FIG. 4A, in a connected state. Also in FIG. 5A, distal body portion 110 is being brought into a position to be connected to a proximal body portion 130. It is to be appreciated that the illustrated embodiment of a proximal body portion includes a plunger 132. Accordingly, upon connection of the proximal body portion to the distal body potion and removal of the tip protector (described below with reference to FIGS. 5B and 6), the injector is ready for delivering of an IOL into a patient's eye. In other embodiments, one or more components (e.g., the plunger may be added to the injector after connection of the proximal body portion to the distal body portion). Typically, as is conventionally known, viscoelastic (not shown) is deposited on the IOL or in the path of the IOL prior to injection of the IOL into a patient's eye. As shown in FIG. 4B, a port 116 may be provided in a wall of distal body portion 110 for adding viscoelastic to the IOL.

Proximal body portion 130 and distal body portion 110 may be configured in any suitable way such that they connect together. For example, the proximal body portion may be press fit together or include one or more snap fit features (not shown). Proximal body portion includes a port 136 that aligns with port 116 (shown in FIG. 4B) so that viscoelastic may be added after connecting of the distal body portion to the proximal body portion.

Figure 5B:
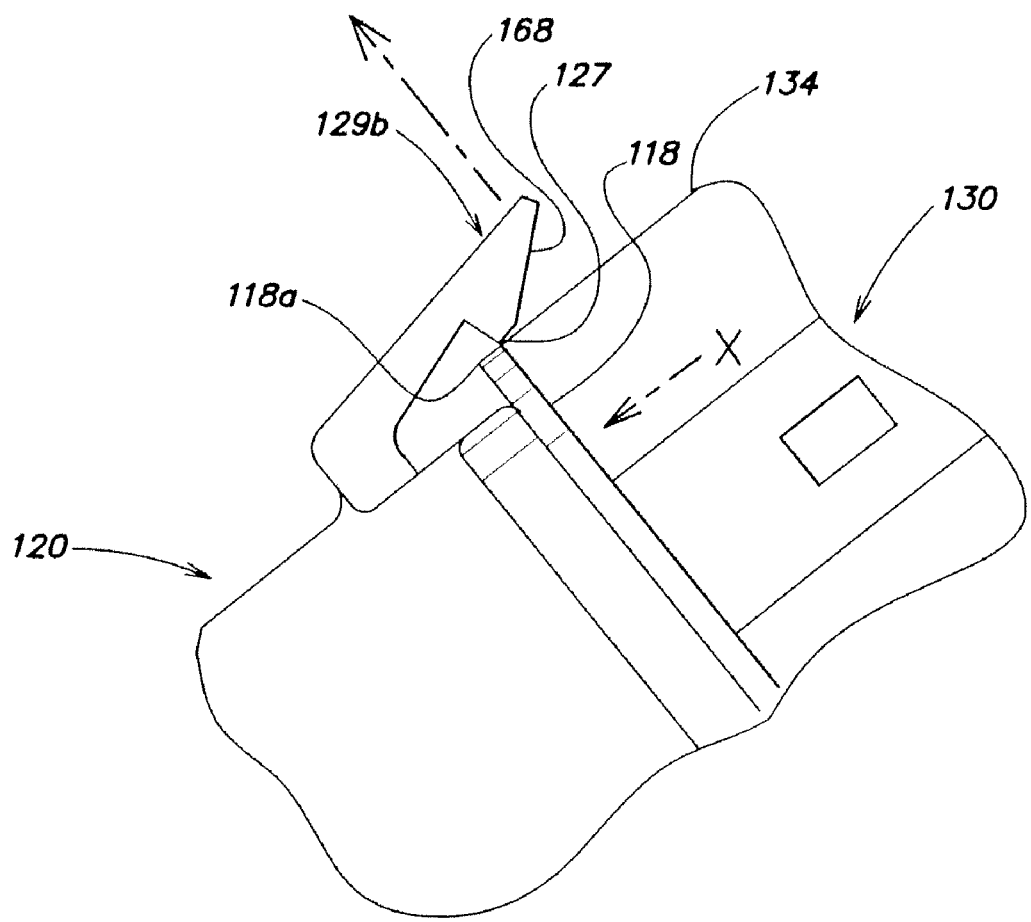
FIG. 5B is an expanded, perspective view of the tip protector and proximal body portion of FIG. 5A interacting with one another to detach the tip protector from the distal body portion, and the proximal body portion and the distal body portion interacting to achieve a connected state.

FIG. 5B is an expanded, perspective view of tip protector 120 and proximal body portion 130 interacting with one another as proximal body portion is being brought into a position to be connected to the distal body portion 110. The interaction between the proximal body portion and the tip protector causes the tip protector to unlock from the distal body portion, such that the tip protector can simply translate away from the distal body portion.

Similar to the description above describing attaching the tip protector to the distal body portion, unlocking the tip protector from distal body portion occurs by flexing the elongate sections 164 of latches 129a and 129b radially outward about pivots 162. However, in FIG. 5B, the flexing is caused by the proximal body portion 130 engaging engagement surface 168. Proximal body portion 130 is configured such that interaction between a wall 134 of the proximal body portion and latch 129b causes the most-radially inward portion 127 of the latch to clear the outermost portion 118a of flange 118 (i.e., the latch 129b and flange 118 are unlocked), and the tip holder can be translated away from the distal body portion.

In the illustrated embodiment, the proximal body portion is translated in a direction X corresponding to the longitudinal direction of the injector to achieve unlocking of the tip protector from the distal body portion. In the illustrated embodiment, the lumen of the proximal body portion and the lumen of the distal body portion are aligned with one another during the translation to achieve the unlocking. However, in other embodiments, the body portions may be configured such that translation to achieve unlocking occurs in a manner such that alignment is not necessary.

Tip protector 120 and proximal body portion 130 may be configured in any suitable way that they interact with one another such that, as discussed above, when the tip protector 120 and the distal body portion 110 are in a connected state, the tip protector is unlocked from the distal body portion as the proximal body portion is being connected to the distal body portion.

It is to be appreciated that, in some embodiments, unlocking of the tip protector from the distal body portion happens simultaneously with the proximal body portion and the distal body portion attaining their final connected positions. In other embodiments, unlocking of the tip protector from the distal body portion happens prior to the proximal body portion and the distal body portion attaining their final connected positions. That is, the unlocking occurs while the connecting is occurring.

Figure 6:
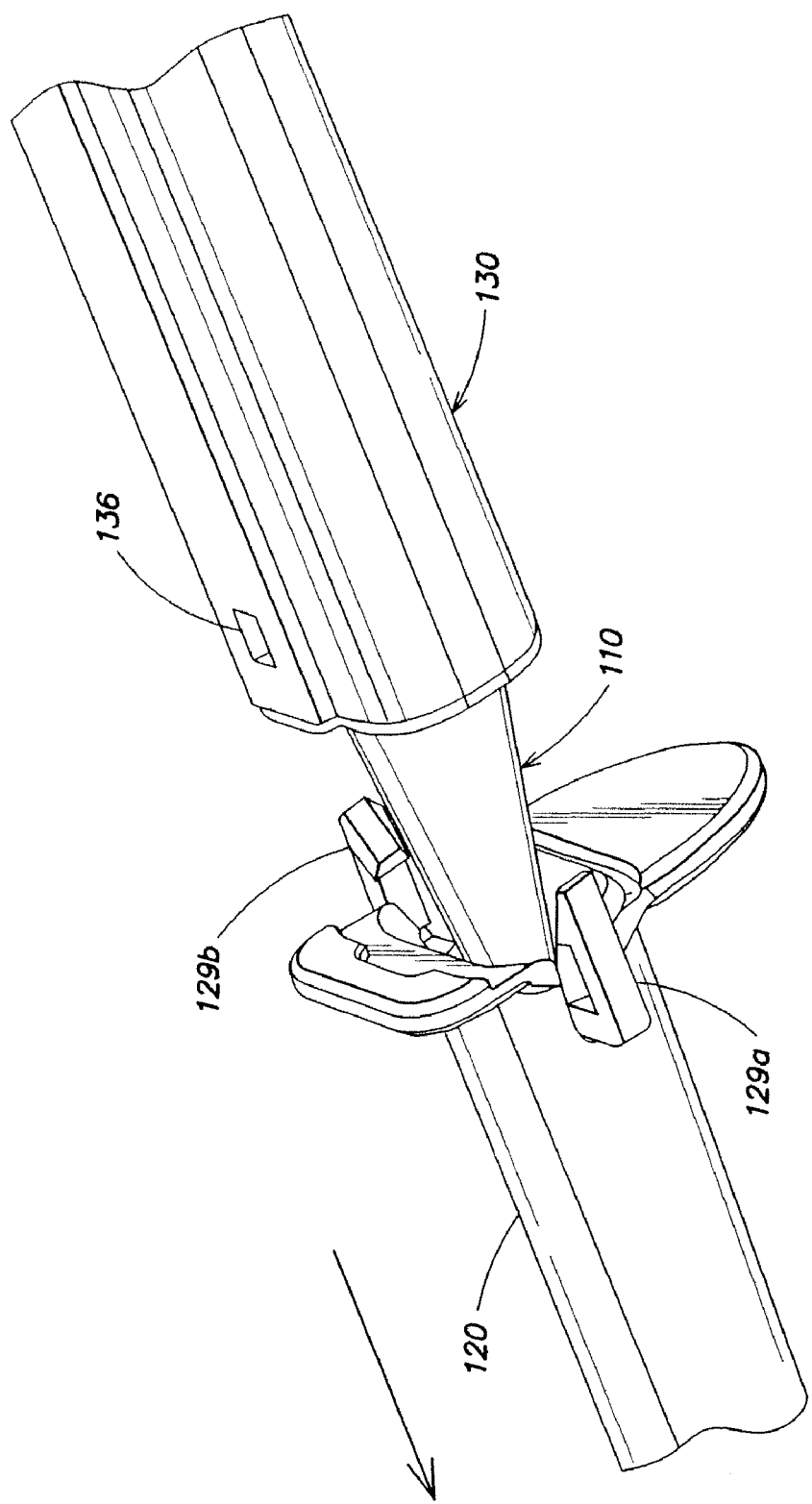
FIG. 6 is a perspective view of the proximal body portion and the distal body portion being in a connected state and the tip protector being removed from the distal body portion.

FIG. 6 is a perspective view of proximal body portion 130 and distal body 110 portion being in a connected state and tip protector 120 being removed from distal body portion 110. It will be appreciated that, upon removal of the tip protector, the injector is ready for injection into a patient's eye.

Having thus described the inventive concepts and a number of exemplary embodiments, it will be apparent to those skilled in the art that the invention may be implemented in various ways, and that modifications and improvements will readily occur to such persons. Thus, the embodiments are not intended to be limiting and presented by way of example only.

The invention is limited only as required by the following claims and equivalents thereto.

What is claimed is:

1. An IOL injector kit, comprising:
   a distal body portion having a longitudinal axis and a length in the direction of the longitudinal axis, the distal body portion comprising a tip configured to permit an IOL to be injected therethrough into an eye;
   a tip protector, the distal body portion and the tip protector being configured to lockingly connect together, the tip protector extending along only a portion of the length of the distal body portion; and
   a proximal body portion configured to connect to the distal body portion, the tip protector and proximal body portion being configured to interact with one another such that, when the tip protector and the distal body portion are in a connected state, the tip protector is caused to be unlocked from the distal body portion by the proximal body portion as the proximal body portion is being connected to the distal body portion.

2. The kit of claim 1, wherein the distal body portion comprises a flange and the tip protector comprises at least one latch, the latch and flange being configured to lockingly connect the distal body portion and the tip protector together.

3. The kit of claim 1, wherein the tip protector comprises a side wall configured to enclose the tip.

4. The kit of claim 1, wherein the tip protector and the distal body portion are lockingly connected together.

5. A method of preparing an IOL injector kit of claim 1 for insertion of an IOL, comprising:
   unlocking a tip protector from a distal body portion by connecting a proximal body portion to the distal body portion.

6. The method of claim 5, further comprising lockingly connecting a tip holder to a distal body portion, prior to the step of unlocking.

7. The method of claim 5, further comprising a step of loading the injector with an IOL prior to the step of unlocking the tip holder from the distal body portion.

8. The method of claim 5, further comprising a step of loading the injector with an IOL after the step of unlocking the tip holder from the distal body portion.

* * * * *